(12) United States Patent
Luengo et al.

(10) Patent No.: US 6,498,155 B1
(45) Date of Patent: Dec. 24, 2002

(54) METHODS OF TREATING THROMBOCYTOPENIA

(75) Inventors: Juan I. Luengo, Audubon, PA (US); Peter I. Lamb, San Diego, CA (US)

(73) Assignees: SmithKline Beecham Corporation, Philadelphia, PA (US); Ligan Pharmaceuticals, San Diego, CA (US)

( * ) Notice: Subject to any disclaimer, the term of this patent is extended or adjusted under 35 U.S.C. 154(b) by 0 days.

(21) Appl. No.: 09/856,248

(22) PCT Filed: Nov. 17, 1999

(86) PCT No.: PCT/US99/27280

§ 371 (c)(1),
(2), (4) Date: Jul. 24, 2001

(87) PCT Pub. No.: WO00/28987

PCT Pub. Date: May 25, 2000

Related U.S. Application Data

(60) Provisional application No. 60/108,808, filed on Nov. 17, 1998.

(51) Int. Cl.[7] .................... A61K 31/33; A61K 31/555
(52) U.S. Cl. ........................ 514/183; 514/184
(58) Field of Search .................. 514/183, 184

(56) References Cited

U.S. PATENT DOCUMENTS

| 5,037,804 A |   | 8/1991  | Nakayasu et al. |
|-------------|---|---------|-----------------|
| 5,126,325 A |   | 6/1992  | Kishimoto et al. |
| 5,583,131 A |   | 12/1996 | Bridger et al. |
| 5,932,546 A | * | 8/1999  | Barrett et al. .................. 514/14 |

FOREIGN PATENT DOCUMENTS

| WO | WO99/11262 | 3/1999 |
| WO | WO99/22733 | 5/1999 |
| WO | WO99/22734 | 5/1999 |

OTHER PUBLICATIONS

De Clercq et al., "Highly Potent and Selective Inhibition of Human Immunodeficiency Virus by the Bicyclam Derivative JM3100" *Antimicrobial Agents and Chemotheraphy*, Apr. 1, 1994, vol. 38, No. 4, pp. 668–674.

* cited by examiner

*Primary Examiner*—Raymond Henley, III
(74) *Attorney, Agent, or Firm*—Wayne J. Dustman; Stephen Venetianer; Charles M. Kinzig

(57) ABSTRACT

Invented are non-peptide TPO mimetics. Also invented is a method of treating thrombocytopenia, in a mammal, including a human, in need thereof which comprises administering to such mammal an effective amount of a linked cyclic polyamine derivative.

12 Claims, No Drawings

METHODS OF TREATING THROMBOCYTOPENIA

This is a 371 of PCT/US 99/27280 filed Nov. 17, 1999 which claim benefit of U.S. provisional application No. 60/108,808 filed Nov. 17, 1998.

FIELD OF THE INVENTION

This invention relates to TPO receptor ligands and their use as agonists of the TPO receptor.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TWO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14:8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369:571–574 (1994); and Sauvage et al., *Nature* 369:533–538(1994). Thrombopoietin is a glycoprotein with two distinct regions separated by a potential Arg-Arg cleavage site. The amino-terminal region is highly conserved in man and mouse, and has some homology with erythropoietin and interferon-alpha and interferon-beta. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoietin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression is restricted to spleen, bone marrow, or fetal liver in mice (see Souyri et al. *Cell* 63: 1137–1147 (1990)) and to megakaryocytes, platelets, and $CD34^+$ cells in humans (see Methia et al. *Blood* 82: 1395–1401 (1993)). Further evidence for TPO-R as a key regulator of megakaryopoiesis is the fact that exposure of $CD34^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration. It would be desirable to provide compounds which allow for the treatment of thrombocytopenia by acting as a TPO mimetic.

International Application PCT/GB92102334 (International Filing date Dec. 16, 1992; WO 93/12096, Published Jun. 24, 1993, hereinafter Bridger) discloses linked cyclic polyamines of Formula (I)

$$Z—R—A—R'—Y \qquad (I)$$

in which Z and Y are independently cyclic polyamine moieties having from 9 to 32 ring members and from 3 to 8 amine nitrogens in the ring spaced by 2 or more carbon atoms from each other;

A is an aromatic or heteroaromatic moiety, and

R and R' are each a substituted or unsubstituted alkylene chain or heteroatom-containing chain which spaces the cyclic polyamines and the moiety A;

as well as acid addition salts and metal complexes thereof.

Bridger does not disclose or claim the compounds of Formula (I) as TPO mimetics or for the treatment of thrombocytopenia.

As disclosed herein it has unexpectedly been discovered that certain small organic molecules, preferably the linked cyclic polyamines of Bridger, are effective as agonist of the TPO receptor, they are potent TPO mimetics.

SUMMARY OF THE INVENTION

This invention relates to a method of treating thrombocytopenia, which comprises administering to a subject in need thereof an effective amount of a TPO mimetic compound of Formula (I).

The present invention also relates to the discovery that the compounds of Formula (I) are active as agonist of the TPO receptor.

Also included in the present invention are methods of co-administering the presently invented TPO mimetic compounds with further active ingredients.

This invention also relates to the discovery that certain non-peptide compounds are effective as TPO mimetics.

DETAILED DESCRIPTION OF THE INVENTION

All publications, including but not limited to patents and patent applications, cited in this specification are herein incorporated by reference as though fully set forth.

The preparation of the compounds of Formula (I) and acid addition salts and metal complexes thereof and formulations thereof is disclosed in International Application PCT/GB92/02334 (International Filing date Dec. 16, 1992; WO 93/12096, Published Jun. 24, 1993, Bridger), the entire disclosure of which is hereby incorporated by reference. In Bridger metal complexes of the claimed linked cyclic polyamine compounds are disclosed as alternative methods for administration, and not disclosed as part of mechanism of activation as anti viral compounds.

By the phrase "non-peptide bifunctional ligand" as used herein is meant a ligand containing two positively-charged regions connected by a linker of 6 to 16 atoms, which is capable of activating the TPO receptor by binding to two non-adjacent sites.

By the term "treating" and derivatives thereof as used herein, is meant prophylatic or therapeutic therapy.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci., USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells in response to TPO.

Some of the most preferred compounds of this invention were also active in an in vitro proliferation assay using the murine 32D-mpl cell line (Bartley, T. D: et al., Cell, 1994, 77, 1117–1124). 32D-mpl cells express Tpo-R and their survival is dependent on the presence of TPO. Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al Science, 1997, 276, 1696–1699).

The pharmaceutically active compounds within the scope of this invention are useful as TPO mimetics in mammals, including humans, in need thereof.

Compounds of Examples 1 and 2 showed activation of over 30% of control (control is the maximal response to TPO) between the concentration range of 10 and 100 uM in the luciferase assay. Compound of Example 1 promoted the proliferation of 32D-mpl cells at concentration 1–30 uM. Compound of Example 1 showed activity in the CD41 megakaryocytic assay at concentrations form 1–30 uM.

The present invention therefor provides a method of treating thrombocytopenia and other conditions with depressed platelet production, which comprises administering a compound of Formula (I):

$$Z-R-A-R'-Y \quad (I)$$

in which Z and Y are independently cyclic polyamine moieties having from 9 to 32 ring members and from 3 to 8 amine nitrogens in the ring spaced by 2 or more carbon atoms from each other.

A is an aromatic or heteroaromatic moiety, and

R and R' are each a substituted or unsubstituted alkylene chain or heteroatom-containing chain which spaces the cyclic polyamines and the moiety A; and acid addition salts and metal complexes thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula I and a pharmaceutically acceptable carrier.

The invention also provides for a pharmaceutical composition for use in the treatment of thrombocytopenia which comprises a compound of Formula I and a pharmaceutically acceptable carrier.

The invention also provides for a pharmaceutical composition for use in enhancing platelet production which comprises a compound of Formula I and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

Preparation of Compound 1-1,1'-[1,4-Phenylenebis(methylene)]bis[1,4.8,11-tetraazacyclotetradecane] octahydrochloride Dihydrate a) 4,8,11 -Tris(p-tolylsulfonyl)-1,4,8,11-tetraazacyclotetradecane A solution of tosyl chloride (8.1 g, 43 mmol) in chloroform (300 mL) was added dropwise over a period of 2 h to a solution of 1,4,8,11-tetraazacyclotetradecane (4.28 g, 21 mmol) in chloroform (150 mL) and triethylamine (18 mL) kept at 45° C. After the mixture stood at room temperature overnight, water (40 mL) was added with stirring. The organic layer was separated, dried ($Na_2SO_4$), and evaporated to dryness. The solid residue was dissolved in hot methanol (40 mL) and cooled to room temperature to yield a white oil. The methanol solution was decanted, and the oil triturated with more methanol to give white crystals of 7-$H_2O$ of the title compound (5.5 g, 33%). A second crop of the tritosyl derivative was obtained by evaporating the mother liquor of the first crop to dryness, dissolving the resulting sticky oil in chloroform (150 mL) and triethylamine (10 mL), and adding to the solution tosyl chloride (2 g, 10 mmol) dissolved in chloroform (50 mL) at 45° C. in 40 min. Standard workup of the solution gave white crystals of 7-$H_2O$ of the title compound (2.1 g, 13%). MS (ESP) m/z 663 $[M+H]^+$.

b) 1,1'-[1,4-Phenylenebis(methylene)]bis[4,8,11-tris(p-tolyisulfonyl)-1,4,8,11-tetraazacyclotetradecane]

To a solution of compound of Example 1(a) (5.5 g, 8. 3 mmol) in acetonitrile (80 mL) were added α,α'-dibromo-p-xylene (1.08 g, 4.1 mmol) and potassium carbonate (3.4 g, 25 mmol). The reaction was heated to reflux for 18 h with rapid stirring. The reaction mixture was allowed to cool to room temperature and concentrated, and the residue was partitioned between methylene chloride and water. The aqueous phase was separated and extracted with two further portions of methylene chloride. The combined organic phases were dried ($MgSO_4$) and evaporated. The residue was washed with methanol to give the title compound as a yellow solid (5.62 g, 89%). MS (ESP) m/z 714 $[M+2H]^{2+}$.

c) 1,1'-[1,4-Phenylenebis(methylene)]bis[1,4,8,11-tetraazacyclotetra-decane]octahydrobromide Dihydrate A rapid stirred solution of compound of Example 1(b) (1.94 g, 1.36 mmol) in 9 mL of acetic acid and 6 mL of hydrobromic acid (Aldrich, 48% aqueous) was heated at 100° C. for 48 h. during which time a crystalline solid precipitated from the brown solution. Upon cooling, the solid was collected by filtration and washed with acetic acid and diethyl ether and dried in vacuo overnight to give the hydrobromide salt of the title compound as a white powder (0.77 g, 48%). MS (ESP) m/z 503 $[M+H]^+$.

d) 1,1'-[1,4-Phenylenebis(methylene)]bis[1,4,8,11-tetraazacyclotetradecane]octaaydrochloride Dihydrate The aqueous solution (5 mL) of hydrobromide salt of the compound Example 1(c) (0.47 g) was neutralized to pH 7 with 1 N of sodium hydroxide. The solution was extracted with 2 mL of methylene chloride . The aqueous layer was neutralized to pH>14, and extracted with methylene chloride. The organic layer was dried ($Na_2SO_4$) and concentrated. The residue was dissolved in 1 ml of ethanol cooled in ice bath. About 1 mL of concentrated hydrochloric acid (Aldrich, 38% aqueous) was added dropwise to give a white precipitate. The precipitate was filtered, washed with ethanol and diethyl ether and dried in vacuo to give the title compound (0.124 g, 38%). MS (ESP) m/z 503 $[M+H]^+$.

Example 2

Preparation of Compound 2-1,1'-[1,3-Phenylenebis(methylene)]bis[1,4,8,11-tetraazacyclotetradecane] octahydrobromide Dihydrate a) 1,1'-[1,3-Phenylenebis(methylene)]bis[4,8,11-tris(p-tolylsulfonyl)-1,4,8,11-tetraazacyclotetradecane]

To a solution of compound of Example 1a (0.98 g, 1.48 mmol) in acetonitrile (40 mL) were added α,α'-dibromo-m-xylene (0.20 g, 0.74 mmol) and potassium carbonate (0.61 g, 4.4 mmol). The reaction was heated to reflux for 18 h with rapid stirring. The reaction mixture was allowed to cool to room temperature and concentrated, and the residue was partitioned between methylene chloride and water. The aqueous phase was separated and extracted with two further portions of methylene chloride. The combined organic phases were dried (MgSO$_4$) and evaporated. The residue was washed with methanol to give the title compound as a yellow solid (0.86 g, 81%). MS (ESP) m/z 714 [M+2H]$^{2+}$ b) 1,1'-[1,3-Phenylenebis(methylene)]bis[1,4,8,11-tetraazacyclotetradecane]octahydrobromide Dihydrate A rapid stirred solution of compound of Example 2a (0.49 g, 0.34 mmol) in 6 mL of acetic acid and 3 mL of hydrobromic acid (Aldrich, 48% aqueous) was heated at 100° C. for 48 h, during which time a crystalline solid precipitated from the brown solution. Upon cooling, the solid was collected by filtration and washed with acetic acid and diethyl ether and dried in vacito overnight to give the title compound as a white powder (0.25 g, 59%). MS (ESP) m/z 503 [M+H]$^+$.

Example 3

Capsule Composition

An oral dosage form for administering a presently invented agonist of the TPO receptor is produced by filing a standard two piece hard gelatin capsule with the ingredients in the proportions shown in Table 1, below.

TABLE I

| INGREDIENTS | AMOUNTS |
| --- | --- |
| 1,1'-[1,4-Phenylenebis(methylene)]bis[1,4,8,11-tetraazacyclotetradecane] octahydrochloride dihydrate (Compound 1) | 25 mg |
| Lactose | 55 mg |
| Talc | 16 mg |
| Magnesium Stearate | 4 mg |

Example 4

Injectable Parenteral Composition

An injectable form for administering a presently invented agonist of the TPO receptor is produced by stirring 1.5% by weight of 1,1'-[1,4-Phenylenebis(methylene)]bis [1,4,8,11-tetraazacyclotetradecane] octahydrochloride dihydrate (Compound I) in 10% by volume propylene glycol in water.

Example 5

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 1,1'-[1,4-Phenylenebis(methylene)]bis[1,4,8,11-tetraazacyclotetradecane] octahydrochloride dihydrate (Compound 1) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating thrombocytopenia in a mammal, including a human, in need thereof which comprises administering to such mammal a therapeutically effective amount of a compound of Formula (I)

$$Z—R—A—R'—Y \quad \text{(I)}$$

in which Z and Y are independently cyclic polyamine moieties having from 9 to 32 ring members and from 3 to 8 amine nitrogens in the ring spaced by 2 or more carbon atoms from each other;

A is an aromatic or heteroaromatic moiety; and

R and R' are each a substituted or unsubstituted alkylene chain or heteroatom-containing chain which spaces the cyclic polyamines and the moiety A, or an acid addition salt or metal complex thereof.

2. The method of claim 1 wherein the compound is 1,1'-[1,4-Phenylenebis(methylene)]bis[1,4,8,11-tetraazacyclotetradecane]; or an acid addition salt or metal complex thereof.

3. The method of claim 1 wherein the compound is 1,1'-[1,3-Phenylenebis(methylene)]bis[1,4,8,11-tetraazacyclotetradecane]; or an acid addition salt or metal complex thereof.

4. A method of enhancing platelet production in a mammal, including a human, in need thereof which comprises administering to such mammal a therapeutically effective amount of a compound of Formula (I)

$$Z—R—A—R'—Y \quad \text{(I)}$$

in which Z and Y are independently cyclic polyamine moieties having from 9 to 32 ring members and from 3 to 8 amine nitrogens in the ring spaced by 2 or more carbon atoms from each other;

A is an aromatic or heteroaromatic moiety; and

R and R' are each a substituted or unsubstituted alkylene chain or heteroatom-containing chain which spaces the cyclic polyamines and the moiety A, or an acid addition salt or metal complex thereof.

5. The method of claim 4 wherein the compound is 1,1'-[1,4-Phenylenebis(methylene)]bis[1,4,8,11-tetraazacyclotetradecane]; or an acid addition salt or metal complex thereof.

6. The method of claim 4 wherein the compound is 1,1'-[1,3-Phenylenebis(methylene)]bis[1,4,8,11-tetraazacyclotetradecane]; or an acid addition salt or metal complex thereof.

7. A method of activating the TPO receptor which comprises administrating non-peptide bifunctional ligand.

8. The method of claim 1 wherein the compound is administered orally.

9. The method of claim 1 wherein the compound is admine paremerally.

10. A method of agonizing the TPO receptor in a subject which comprises administering an effective amount of a compound of Formula (I),

(I)

in which Z and Y are independently cyclic polyamine moieties having from 9 to 32 ring members and from 3 to 8 amine nitrogens in the ring spaced by 2 or more cabon atoms from each other;

A is an aromatic or heteroaromatic moiety; and

R and R' are each a substituted or unsubstituted alkylene chain or heteroatom-containing chain which spaces the cyclic polyamines and the moiety A, or an acid addition salt or metal complex thereof.

11. A method of agonizing the TPO receptor in a subject which comprises administering an effective amount of a non-peptide TPO mimetic.

12. A method of enhancing platelet production in a subject comprising administering to said subject a therapeutically effective amount of a non-peptide TPO receptor agonist.

* * * * *